(12) United States Patent
Eccleson et al.

(10) Patent No.: US 6,348,188 B1
(45) Date of Patent: Feb. 19, 2002

(54) WASHING COMPOSITIONS

(75) Inventors: Graham Charles Eccleson; Peter Fairley, both of Wirral (GB); Stanley Lam, Pleasant Hill, CA (US)

(73) Assignee: Unilever Home & Personal Care USA, Chicago, IL (US)

( * ) Notice: Subject to any disclaimer, the term of this patent is extended or adjusted under 35 U.S.C. 154(b) by 0 days.

(21) Appl. No.: 09/456,003

(22) Filed: Dec. 7, 1999

(30) Foreign Application Priority Data

Dec. 10, 1998 (GB) .............................. 9827224

(51) Int. Cl.$^7$ ............................ A61K 7/075; A61K 7/08
(52) U.S. Cl. ................. 424/70.19; 424/70.1; 424/70.6; 424/70.11; 424/70.12; 424/70.13; 424/70.15; 424/70.16; 424/70.21; 424/70.22; 424/70.23; 424/70.24; 424/70.31
(58) Field of Search .............................. 424/70.1, 70.11, 424/70.22, 70.23, 70.24, 70.21, 70.31, 70.12, 70.6, 70.16, 70.15, 70.13, 70.19

(56) References Cited

FOREIGN PATENT DOCUMENTS

| EP | 0432951 | * | 6/1991 | ......... A61K/7/075 |
|---|---|---|---|---|
| EP | 0498119 | * | 8/1992 | ............ A61K/7/11 |
| GB | 1111708 | * | 5/1968 | ............ C11D/5/00 |
| GB | 1228060 | * | 4/1971 | ............ C11D/1/02 |
| WO | 95/22311 | * | 8/1995 | ............ A61K/7/50 |
| WO | 96/17592 | * | 6/1996 | ............ A61K/7/50 |
| WO | 97/48375 | * | 12/1997 | ............ A61K/7/48 |
| WO | 97/48378 | * | 12/1997 | ............ A61K/7/50 |
| WO | 9748378 |   | 12/1997 |                       |
| WO | 98/18432 | * | 5/1998 | ............ A61K/7/06 |

OTHER PUBLICATIONS

International Search Report Application No. PCT/EP 99/09328

* cited by examiner

Primary Examiner—Thurman K. Page
Assistant Examiner—Humera N. Sheikh
(74) Attorney, Agent, or Firm—Matthew Boxer

(57) ABSTRACT

A shampoo composition having at least one detersive surfactant, a suspending particulate agent, and a cationic deposition polymer, wherein at least about 5% by weight of the cationic deposition polymer is adsorbed on the suspended particulate agent is described.

9 Claims, No Drawings

WASHING COMPOSITIONS

FIELD OF THE INVENTION

This invention relates to washing compositions. More particularly the invention relates to washing compositions which contain a cationic polymer and a suspended particulate agent, and which provide enhanced deposition and delivery of the suspended particulate agent. Such washing compositions include compositions for washing hair or skin, such as hair shampoos and conditioners, body shampoos, shower gels, facial washing compositions and bath foams.

BACKGROUND AND PRIOR ART

Difficulties arise in achieving effective deposition of suspended particulate agents, such as conditioning agents, onto a surface such as skin or hair when the agent is delivered by means of incorporation into rinse-off compositions, typically hair and body shampoos, conditioners and the like. Frequently, such suspended particulate agents are preferentially rinsed away from the intended site of deposition, rather than being deposited thereat.

Cationic deposition polymers are known to enhance deposition of certain components from shampoos and other personal cleansing compositions. For example, U.S. Pat. Nos. 5,037,818 and 5,085,857 describe the use of cationic guar gum to enhance the deposition of particulate antimicrobials and insoluble silicone respectively. Deposition polymers have also been proposed to enhance the deposition of sunscreen materials from a shampoo composition. In EP 386 898 a cationic polygalactomannan gum derivative is used. WO 95/22311 describes the use of certain cationic polyacrylamide polymers to increase the deposition of conditioning agents which include silicones, fats and oils, waxes, hydrocarbons, fatty acids and fatty alcohols, lipids, vitamins and sunscreens. WO97/48378 is directed to a process for preparing liquid personal cleansing compositions which provide enhanced deposition of a volatile perfume. The process involves forming a premix comprised of a cationic polymer, a volatile perfume and water, and then adding the premix to a personal cleansing base composition containing an anionic surfactant. In this process, it is believed that the volatile perfume becomes physically entrapped within coacervates or ion-pairs formed between the cationic polymer and the anionic surfactant present in the composition.

A problem associated with cationic polymer aided deposition of materials is that although the cationic polymers are effective deposition aids for a wide variety of materials (as can be seen from the art above), they tend to be indiscriminate in what they deposit. It is thought that this indiscriminacy is due to the physical entrapment mechanism postulated in WO97/48378. This reduces the efficiency of deposition of the ingredients it is desired to deposit (e.g. conditioning agents such as silicone) and can also lead to dulling of the hair through excessive build-up.

The present inventors have found that this problem can be solved by preadsorbing the cationic polymer onto the particular suspended particulate agent which it is desired to deposit. Surprisingly, the adsorbates so formed are stable towards the presence of surfactant.

SUMMARY OF THE INVENTION

The present invention provides a washing composition comprising, in an aqueous carrier:
a) at least one detersive surfactant selected from the group consisting of anionic surfactants, amphoteric surfactants which have been altered to have a negative charge, and mixtures thereof, and
b) a suspended particulate agent having a cationic deposition polymer adsorbed thereon;
in which the proportion of cationic polymer adsorbed to the suspended particulate agent is at least 5% by weight based on the total weight of cationic polymer present in the composition.

In a second aspect, the present invention provides a process for preparing a washing composition as defined above, which process comprises the steps of;
(i) adsorbing the cationic deposition polymer onto the suspended particulate agent, and
(ii) blending the adsorbate so obtained with a base washing composition comprising, in an aqueous carrier, the at least one detersive surfactant as described above.

DETAILED DESCRIPTION AND PREFERRED EMBODIMENTS

(I) Detersive Surfactant

The washing compositions of the invention contain at least one detersive surfactant selected from the group consisting of anionic surfactants, amphoteric surfactants which have been altered to have a negative charge, and mixtures thereof.

Anionic Surfactant

Suitable anionic surfactants for washing compositions of the invention include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates and acyl methyl taurates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionics include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, and sodium N-lauryl sarcosinate.

Amphoteric Surfactant

An amphoteric surfactant which has been altered to have a negative charge can be used in the washing composition of the invention instead of the anionic surfactant or in combination with the anionic surfactant. The charge of the amohoteric surfactant can be altered by conventional means, for example, by adjusting the pH of a surfactant solution containing the amphoteric surfactant.

Amohoteric surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates and alkyl amidopropyl hydroxysultaines. Examples include lauryl amine oxide, cocodimethyl sulphopropyl betaine and preferably lauryl betaine, cocamidopropyl betaine and sodium cocamphopropionate.

The level of anionic or negatively-charged amphoteric surfactant in washing compositions of the invention is generally from 3 to 50%, preferably from 3 to 30%, more preferably from 5% to 20% by weight of the total composition. The anionic or negatively charged amphoteric surfactant may be used in combination with other natural or synthetic co-surfactants. The optional co-surfactant is typically selected from the group consisting of: nonionic surfactants, amphoteric surfactants, cationic surfactants and mixtures thereof.

Further surfactant may also be present as emulsifier for emulsified components of the washing composition, e.g. emulsified particles of silicone. This may be the same surfactant as the detersive surfactant, or may be different.

Suitable emulsifying surfactants are well known in the art and include anionic and nonionic surfactants. Examples of anionic surfactants used as emulsifiers for materials such as silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers for materials such as silicone particles are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

The total level of surfactant in washing compositions of the invention is generally from 3 to 50%, preferably from 5 to 30%, more preferably from 10% to 25% by weight of the total composition.

(II) Suspended Particulate Agent

The suspended particulate agent may suitably be selected from one or more of the following classes of material:
Conditioning Agents As used herein, the term "conditioning agent" includes any material which is used to give a particular conditioning benefit to hair and/or skin. For example, in washing compositions for use on the skin such as body shampoos materials such as moisturisers, essential oils, sun-protective or after-sun treatment materials, occlusive oils and the like may be used. In washing compositions for use on the hair, such as hair shampoos and conditioners, suitable materials are those which deliver one or more benefits relating to shine, softness, combability, wet-handling, anti-static properties, protection against damage, body, volume, stylability and manageability.

Preferred conditioning agents for use in the present invention include emulsified silicones, used to impart for example wet and dry conditioning benefits to hair such as softness, smooth feel and ease of combability.

Various methods of making emulsions of particles of silicones for use in the invention are available and are well known and documented in the art.

The viscosity of the silicone itself (not the emulsion or the final washing composition) preferably ranges from 10,000 cps to 5 million cps. The viscosity can be measured by means of a glass capillary viscometer as set out further in Dow Corning Corporate Test Method CTM004 Jul. 20, 1970.

Suitable silicones include polydiorganosiloxanes, in particular polydimethylsiloxanes which have the CTFA designation dimethicone. An example is dimethicone fluid having a viscosity of up to 100,000 centistokes at 25° C., which is available commercially from the General Electric Company as the Viscasil series and from Dow Corning as the DC 200 series.

Aminofunctional silicones which have the CTFA designation amodimethicone, are also suitable for use in the compositions of the invention, as are polydimethyl siloxanes having hydroxyl end groups, which have the CTFA designation dimethiconol.

Also suitable are silicone gums. "Silicone gum" denotes polydiorganosiloxanes having a molecular weight of from 200,000 to 1,000,000 and specific examples include dimethicone gums, dimethiconol gums, polydimethyl siloxane/diphenyl/methylvinylsiloxane copolymers, polydimethylsiloxane/methylvinylsiloxane copolymers and mixtures thereof. Examples include those materials described in U.S. Pat. No. 4,152,416 (Spitzer), and on General Electric Silicone Rubber product Data Sheet SE 30, SE 33, SE 54 and SE 76.

Also suitable for use in the present invention are silicone gums having a slight degree of cross-linking, as are described for example in WO 96/31188. These materials can impart body, volume and stylability to hair, as well as good wet and dry conditioning.

Preferred emulsified silicones for use in washing compositions of the invention have an average silicone particle size in the washing composition of less than 30 microns. Particle size may be measured by means of a laser light scattering technique, using a 2600D Particle Sizer from Malvern Instruments.

The average particle size of the silicone material in the washing composition may for example range from 2 to 30 microns, preferably from 2 to 20 microns, more preferably 3 to 10 microns.

Alternatively the silicone material may be present in the washing composition in the form of emulsified particles of small size, for example less than 2 microns. Reducing the particle size may under some circumstances improve conditioning performance.

Silicone emulsions having an average silicone particle size of ≦0.15 microns are generally termed microemulsions. Typically such microemulsified particles will have a particle size of ≦0.15 microns, suitably from 0.01 to 0.15 microns. These may be advantageous since they enable the formulation of washing compositions of high stability and excellent optical properties such as translucent or transparent formulations.

Suitable silicone emulsions for use in the invention are commercially available in a pre-emulsified form. This is particularly preferred since the pre-formed emulsion can be incorporated into the washing composition by simple mixing.

Typically, a pre-formed emulsion will contain around 50% of silicone. Pre-formed emulsions are available from suppliers of silicone oils such as Dow Corning, General Electric, Union Carbide, Wacker Chemie, Shin Etsu, Toshiba, Toyo Beauty Co, and Toray Silicone Co. Examples of larger particle size silicone emulsions (around 3 to 20 micron average particle size in the emulsion ) are the material sold as DC-1310 by Dow Corning, and the materials sold as X-52-1086, X-52-2127 and X-52-2112 by Shin-Etsu.

Examples of suitable pre-formed emulsions of smaller particle size (less than about 2 micron average particle size in the emulsion) include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

The amount of silicone incorporated into the washing compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

When the silicone is incorporated as a pre-formed emulsion as described above, the exact quantity of emulsion will of course depend on the concentration of the emulsion, and should be selected to give the desired quantity of insoluble, non-volatile silicone in the final composition.

A further preferred class of conditioning agents are per-alk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into the washing compositions of the invention depends on the level of body and volume enhancement desired and the specific material used. A preferred amount is from 0.01 to about 10% by weight of the total composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight of the total composition is a particularly suitable level.

Solid Active Agents

Examples of typical solid active agents include antimicrobials such as the heavy metal salts of pyridinethione, especially zinc pyridinethione, other antimicrobials such as climbazole, piroctone olamine, selenium sulphide and ketoconazole. These substances typically have an average particle diameter of from about 0.2 to about 50 microns, preferably from about 0.4 to about 10 microns.

Where the solid active agent is an antimicrobial agent, such as zinc pyridinethione, this may be suitably be employed in the composition in an amount of from 0.001% to about 1% by weight of the total composition.

Other suitable solid active agents include pigment particles, such as solid dyes or colorants suitable for application to hair, and metal colloids.

Aesthetic Agents

Hair treatment compositions such as shampoos and conditioners are frequently opacified or pearlised to enhance consumer appeal.

Examples of opacifying agents include higher fatty alcohols (e.g. cetyl, stearyl, arachidyl and behenyl), solid esters (e.g. cetyl palmitate, glyceryl laurate, stearamide MEA-stearate), high molecular weight fatty amides and alkanolamides and various fatty acid derivatives such as propylene glycol and polyethylene glycol esters. Inorganic materials used to opacify hair treatment compositions include magnesium aluminium silicate, zinc oxide, and titanium dioxide.

Pearlescing agents typically form thin, platelet-type crystals in the composition, which act like tiny mirrors. This gives the pearl lustre effect. Some of the opacifying agents listed above may also crystallise as pearlescing agents, depending on the media in which they are used and the conditions employed.

Typical pearlescing agents may be selected from C16–C22 fatty acids (e.g. stearic acid, myristic acid, oleic acid and behenic acid), esters of C16–C22 fatty acid with alcohols and esters of C16–C22 fatty acid incorporating such elements as alkylene glycol units. Suitable alkylene glycol units may include ethylene glycol and propylene glycol. However, higher alkylene chain length glycols may be employed. Suitable higher alkylene chain length glycols include polyethylene glycol and polypropylene glycol.

Examples are polyethylene glycol mono or diesters of C16–C22 fatty acids having from 1 to 7 ethylene oxide units, and ethylene glycol esters of C16–C22 fatty acids. Preferred esters include polyethylene glycol distearates and ethylene glycol distearates. Examples of a polyethylene glycol distearate available commercially are EUPERLAN PK900 (ex Henkel) or GENAPOL TS (ex Hoechst). An example of an ethylene glycol distearate is EUPERLAN PK3000 (ex Henkel).

Other pearlescing agents include alkanolamides of fatty acids having from 16 to 22 carbon atoms, (e.g. stearic monoethanolamide, stearic diethanolamide, stearic monoisopropanolamide and stearic monoethanolamide stearate); long chain esters of long chain fatty acids (e.g. stearyl stearate, cetyl palmitate); glyceryl esters (e.g. glyceryl distearate),long chain esters of long chain alkanolamides (e.g. stearamide DEA distearate, stearamide MEA stearate), and alkyl (C18–C22) dimethyl amine oxides (e.g. stearyl dimethyl amine oxide).

Further suitable pearlescing agents include inorganic materials such as nacreous pigments based on the natural mineral mica. An example is titanium dioxide coated mica. Particles of this material may vary in size from 2 to 150 microns in diameter. In general, smaller particles give rise to a pearly appearance, whereas particles having a larger average diameter will result in a glittery composition.

Suitable titanium dioxide coated mica particles are those sold under the trade names TIMIRON (Merck) or FLAMENCO (Mearl).

The level of opacifying or pearlescing agent employed in compositions of the invention is generally from 0.01 to 20%, preferably 0.01 to 5%, more preferably from 0.02 to 2% by weight of the total composition.

(III) Cationic Deposition Polymer

By "deposition polymer" is meant an agent which enhances deposition of the conditioning agent from the washing composition of the invention onto the intended site during use, i.e. the hair and/or the scalp.

The deposition polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

- copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J. USA) under the LUVIQUAT tradename (e.g. LUVIQUAT FC 370);
- copolymers of 1-vinyl-2-pyrrolidine and dimethylaminoethyl methacrylate, referred to in the industry (CTFA) as Polyquaternium-11. This material is available commercially from Gaf Corporation (Wayne, N.J. USA) under the GAFQUAT tradename (e.g., GAFQUAT 755N);
- cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl esters of homo-and co-polymers of unsaturated carboxylic acids having from 3 to 5 carbon atoms, (as described in U.S. Pat. No. 4,009,256);
- cationic polyacrylamides(as described in WO95/22311). Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

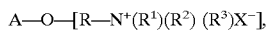

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J. USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J. USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17(high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives.

Particularly preferred deposition polymers are JAGUAR C13S, JAGUAR C15, JAGUAR C17 and JAGUAR C16 and JAGUAR C162.

The Adsorbate

Key to the present invention is the adsorption of the cationic deposition polymer to the suspended particulate agent. The inventors have found that adsorbates can be formed which are surprisingly stable towards the addition of surfactant and which can facilitate preferential deposition of the suspended particulate agent from the washing composition when it is diluted during use.

One convenient way of preparing the adsorbate of cationic deposition polymer and suspended particulate agent is by:

(i) preparing an aqueous solution of the cationic deposition polymer;

(ii) adding the suspended particulate agent to the resulting solution;

(iii) adjusting the pH of the solution so that the cationic deposition polymer becomes at or near to its isoelectric point, mixing and then readjusting the pH of the mixture so as to recharge the cationic deposition polymer.

By the phrase "near its isoelectric point" it is generally meant that the cationic polymer is within 1 to 1.5 pH units of its isoelectric point. The isoelectric point will depend on the particular cationic polymer used.

When recharged after step (iii) described above, the cationic charge density of the cationic deposition polymer, which is defined as the moles of cationic charge per gram of polymer, should typically be at least 0.1 meq/g, preferably above 0.8 or higher. The cationic charge density should typically not exceed 4 meq/g. It is preferably less than 3 and more preferably less than 2 meq/g. The charge density can be measured using conductimetric analysis.

For example, a preferred cationic deposition polymer is JAGUAR C13S which will typically have a cationic charge density when recharged of about 0.8meq/g.

Following the method as described above for the material JAGUAR C13S, we have found that particularly durable adsorbates can be formed with silicone droplets as the suspended particulate agent, by:

(i) preparing an aqueous solution (suitably about 1wt %) or the JAGUAR C13S at pH above 8, (preferably about 9);

(ii) adding the silicone droplets;

(iii) adjusting the mixture to pH 4–7, (preferably about 6), mixing for about 20 minutes, and then readjusting the pH of the mixture to above 8, (preferably about 9).

The total amount of cationic deposition polymer in the washing composition generally ranges from 0.005 to 2%, preferably from 0.01 to 1.0%, optimally from 0.03 to 0.8% by weight of the total composition.

By "total amount" is meant that which is adsorbed to the suspended particulate agent and in addition any free cationic deposition polymer, if this is present.

By "free cationic deposition polymer" is meant cationic deposition polymer which is not adsorbed to the suspended particulate agent in the washing composition.

In washing compositions according to the invention, it is required that the proportion of cationic polymer adsorbed to the suspended particulate agent is at least 5% by weight based on the total weight of cationic polymer present in the composition. Preferably this proportion is at least 30%, more preferably at least 40% and optimally at least 50%.

(IV) Aqueous Carrier

The washing compositions of the present invention contain an aqueous carrier. The carrier of the composition of the invention is predominantly water, but non-aqueous solvents also can be used in order to help solubilise ingredients that are not sufficiently soluble in water. Suitable non-aqueous solvents include the lower alcohols like ethyl alcohol and propyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether and mixtures thereof.

The total level of water in the final washing composition ranges in general from 20% to 99%, preferably from 40 to 90%, more preferably from 60% to 90%, ideally from 70% to 90%, by weight of the total composition.

(V) Optional Ingredients

Depending on the type of composition employed, one or more additional ingredients conventionally incorporated into personal care formulations may be included in the compositions of the invention. Such additional ingredients include opacifiers such as polyethylene glycol distearate and ethylene glycol stearates, polymer lazices, additional anti-microbial agents such as ZnPTO and Octopirox, foam boosters, perfumes, colouring agents, preservatives, viscosity modifiers, proteins, polymers, buffering or pH adjusting agents, moisturising agents, herb or other plant extracts and other natural ingredients.

Each of these ingredients will be present in an amount effective to accomplish its purpose. Generally these optional ingredients are included individually at a level of up to about 5% by weight of the total composition.

Preferably, compositions of this invention intended for hair treatment also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are: ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

(VI) Use of the washing composition

The washing compositions of the invention may take any suitable form appropriate to the suspended particulate agent which they contain and are intended to deposit. By suitable selection of essential and non-essential ingredients and relative amounts thereof, the washing compositions of the invention may be in the form of, for example, hair shampoos and conditioners and other rinse-off hair treatment compositions, body shampoos, shower gels, facial washing compositions, bath foams and the like.

Preferred compositions in the form of body or hair shampoos may be applied to the skin or hair, as appropriate, and worked to create a lather. The lather may be retained at the applied site for a short time, e.g. one or several minutes, before rinsing, or may be immediately rinsed. The procedure may be repeated if desired.

Retention of the lather at the site of application and repetition of the application regime may be of additional benefit in enhancing even further the amount or rate of deposition of the suspended particulate agent on the skin or hair surface, and/or its delivery to the hair follicle.

The invention is further illustrated by the following non-limiting Example.

EXAMPLE

A shampoo composition was prepared having ingredients as shown in the following Table:

| Ingredient | Active amount (wt %) | Tradename & supplier |
| --- | --- | --- |
| sodium lauryl ether sulphate | 14 | Empicol ESB 70 (Albright and Wilson) |
| cocamidopropylbetaine | 2 | Tegobetaine CK (Goldschmidt) |
| guar hydroxypropyltrimonium chloride | 0.03 | Jaguar C13S (Rhodia) |
| dimethiconol microemulsion | 0.8 | DC2-1391 (Dow Corning) |
| sodium chloride | 0.5 | |
| water | to 100 | |

The method of preparation of the shampoo is as follows: For 100 g of shampoo, dissolve 0.018 g of guar hydroxypropyltrimonium chloride in the free water of the formulation and adjust the pH to 9. Add the dimethiconol microemulsion and stir well for twenty minutes. Adjust the pH of the mixture to 6 and then combine it with the other components of the formulation and the remaining guar hydroxypropyltrimonium chloride.

What is claimed is:

1. A washing composition comprising, in an aqueous carrier:
   a) at least one detersive surfactant selected from the group consisting of anionic surfactants, amphoteric surfactants which have been altered to have a negative charge, and mixtures thereof, and
   b) a suspended particulate agent having a cationic deposition polymer adsorbed thereon;
   in which the proportion of cationic polymer adsorbed to the suspended particulate agent is at least 5% by weight based on the total weight of cationic polymer present in the composition.

2. A washing composition according to claim 1, in which the detersive surfactant is selected from the group consisting of alkyl sulphates, alkyl ether sulphates and mixtures thereof.

3. A washing composition according to claim 2, in which the suspended particulate agent is an emulsified silicone or a per-alk(en)yl hydrocarbon material.

4. A washing composition according to claim 3, in which the cationic deposition polymer is selected from cationic cellulose and cationic guar derivatives.

5. A washing composition according to claim 1, which is in the form of a hair or body shampoo.

6. A process for preparing a washing composition as defined above, which process comprises the steps of;
   (i) adsorbing the cationic deposition polymer onto the suspended particulate agent, and
   (ii) blending the adsorbate so obtained with a base washing composition comprising, in an aqueous carrier, the at least one detersive surfactant as described above.

7. A process according to claim 6, in which the adsorbate of cationic deposition polymer and suspended particulate agent is prepared by the following method:
   (i) preparing an aqueous solution of the cationic deposition polymer;
   (ii) adding the suspended particulate agent to the resulting solution;
   (iii) adjusting the pH of the solution so that the cationic deposition polymer becomes at or near to its isoelectric point, mixing and then readjusting the pH of the mixture so as to recharge the cationic deposition polymer.

8. A washing composition comprising, in an aqueous carrier:
   (a) at least one detersive surfactant selected from the group consisting of anionic surfactant, amphoteric surfactants which have been altered to have a negative charge, and mixtures thereof; and
   (b) a suspended particulate agent which is silicone droplets;
   in which the proportion of cationic polymer adsorbed to the silicone droplets is at least 5% by weight based on the total weight of cationic polymer present in the composition.

9. A durable adsorbate with silicone droplets and Jaguar C-13S prepared by:
   (a) preparing an aqueous solution of Jaguar C-13S at a pH above 8;
   (b) adding silicone droplets;
   (c) adjusting pH to 4 to 7, and mixing for about 20 minutes, and then readjusting pH to above 8.

* * * * *